US00PP30026P2

(12) United States Plant Patent
Jones

(10) Patent No.: US PP30,026 P2
(45) Date of Patent: Dec. 25, 2018

(54) ***DIANTHUS* PLANT NAMED 'DCACR08-0'**

(50) Latin Name: *Dianthus hybrida*
Varietal Denomination: DCACR08-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 15/731,665

(22) Filed: Jul. 12, 2017

(51) Int. Cl.
*A01H 5/02* (2018.01)

(52) U.S. Cl.
USPC ..... Plt./277

(58) Field of Classification Search
USPC ..... Plt./277
See application file for complete search history.

*Primary Examiner* — Annette H Para
(74) *Attorney, Agent, or Firm* — Cassandra Bright

(57) ABSTRACT

A new and distinct *Dianthus* cultivar named 'DCACR08-0' is disclosed, characterized by continuous flowering on floriferous plants hardy to USDA Zone 3. Flowers are semi-double and bright, dark pink. The new variety is a *Dianthus*, typically produced as a garden or container plant.

2 Drawing Sheets

Latin name of the genus and species: *Dianthus hybrida.* Variety denomination: 'DCACR08-0'.

BACKGROUND OF THE INVENTION

The new cultivar is a product of chance discovery. The new variety originated as a spontaneous whole plant mutation discovered among a commercial planting of mixed *Dianthus hybrida* varieties. The parent is unknown. 'DCACR08-0' was discovered by the inventor, Steve Jones, at a commercial greenhouse in Santa Paula, Calif. during Summer of 2014.

Asexual reproduction of the new cultivar 'DCACR08-0' was first performed in Santa Paula, Calif. at a commercial greenhouse by vegetative cuttings in Summer of 2014. 'DCACR08-0' has since produced several generations and has shown that the unique features of this cultivar are stable and reproduced true to type.

SUMMARY OF THE INVENTION

The cultivar 'DCACR08-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCACR08-0'. These characteristics in combination distinguish 'DCACR08-0' as a new and distinct *Dianthus* cultivar:

1. Floriferous plants.
2. Suitability for both garden and container uses.
3. Dark and bright pink flower colored near Red-Purple 61A with a white petal base.
4. Continuous flowering from Spring through Fall. Repeat flowering enhanced by removal of spent flowers.
5. Hardy to USDA zone 3
6. Semi-double flower with an average of 15 to 20 petals.

COMMERCIAL COMPARISON

Plants of the new cultivar 'DCACR08-0' are comparable to the commercial *Dianthus* variety 'DCACR06-0', filed concurrently. The two *Dianthus* varieties are similar in most horticultural characteristics; however, the new variety 'DCACR08-0' produces a flower with a different red-purple color, mainly darker and having less purple tones.

Plants of the new cultivar 'DCACR08-0' can also be compared to the commercial *Dianthus* variety 'DDTHP02-0', U.S. Plant Pat. No. 28,102. These varieties are similar in most horticultural characteristics; however 'DCACR08-0' produces a dark red-purple flower, compared to the lighter purple flower of this comparator.

BRIEF DESCRIPTION OF THE PHOTOGRAPHS

Figure 1:
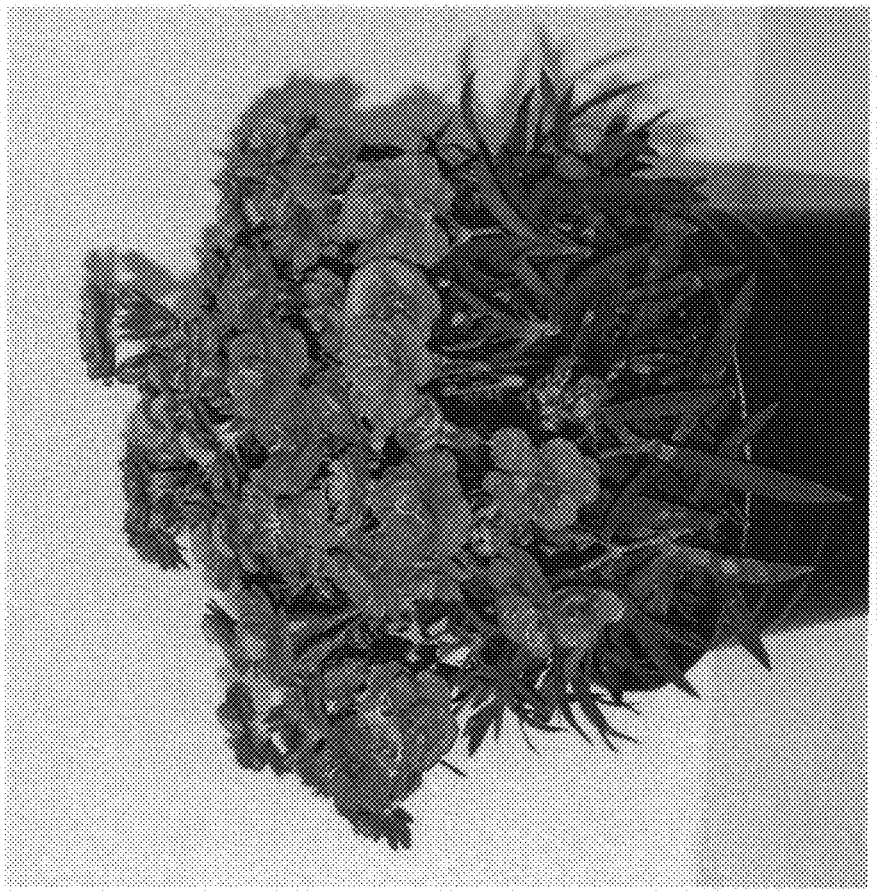

The accompanying photograph in FIG. 1 illustrates in full color a typical plant of 'DCACR08-0' grown outdoors in Santa Paula, Calif. This plant is approximately 20 weeks old, shown in a 1 gallon pot.

Figure 2:
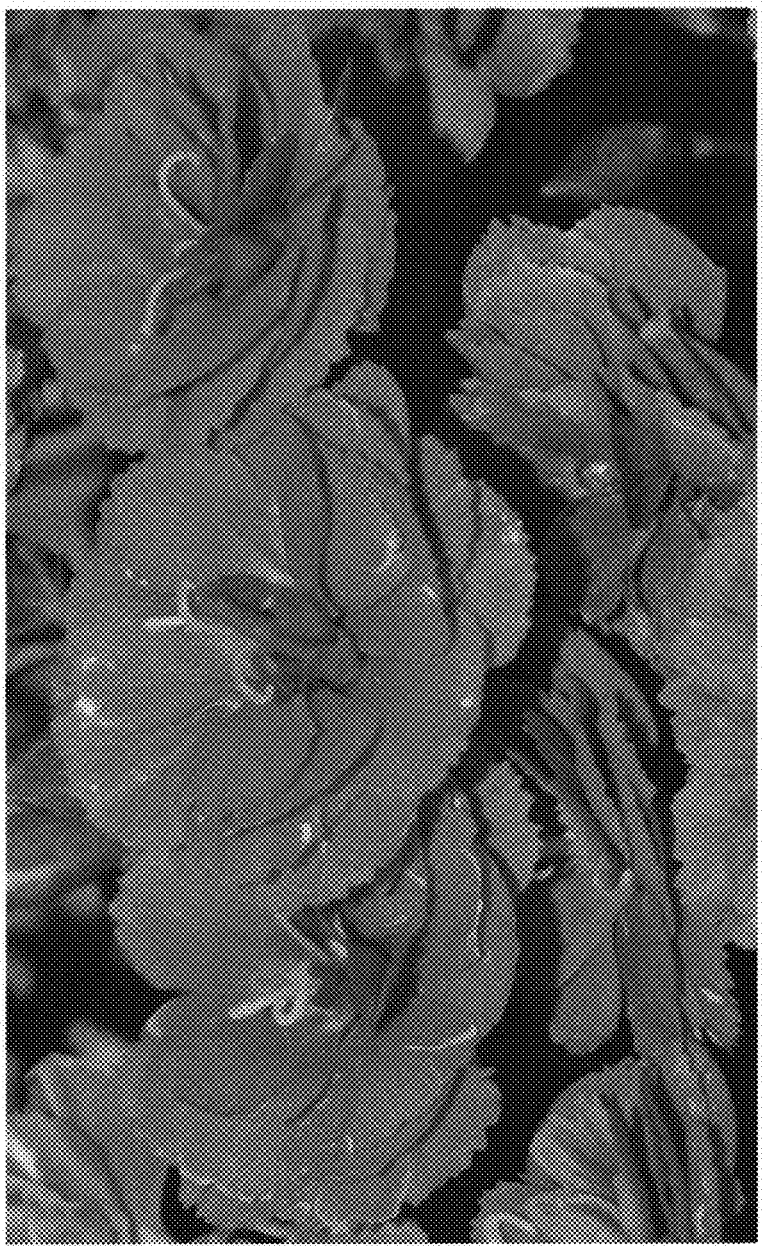

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DCACR08-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus hybrida* 'DCACR08-0'.

PROPAGATION

Time to initiate roots: About 10 days at approximately 24° C.

Time to produce a rooted cutting: About 18 days at 24 ° C.
Root description: Fibrous roots, approximately 1 to 3 mm in diameter, colored near Orange-White 159C.

PLANT

Age of plant described: Approximately 20 weeks from rooted cutting.
Pot size: 1 gallon.
Plant type: Compact upright perennial.
Plant habit: Upright growing stems emerge basally.
Plant spread: Approximately 24 cm.
Height: Approximately 21 cm to top of flowering plane. Approximately 12 cm to top of foliar plane.
Length plant stem: Average range 9 to 11 cm.
Diameter of plant stem: Approximately 0.3 cm.
Quantity stems: Approximately 35.
Stem:
*Color*.—Near RHS Green 138A.
*Texture*.—Smooth.
Internode length: Average 3.5 cm.
*Shape*.—Round.
*Solid or hollow*.—Solid.

FOLIAGE

Leaf:
*Node diameter*.—4 mm.
*Node length*.—3 mm.
*Arrangement*.—Opposite (in pairs).
*Quantity*.—Approximately 6-10 fully expanded per stem. Average range of 2 to 6 immature leaves per stem.
*Average length*.—Approximately 5.2 cm.
*Average width*.—Approximately 0.7 cm.
*Shape of blade*.—Linear.
*Apex*.—Acute.
*Base*.—Clasping.
*Attachment*.—Sessile.
*Margin*.—Entire.
*Texture of top surface*.—Smooth.
*Texture of bottom surface*.—Smooth.
*Pubescence*.—None.
*Color*.—Young foliage upper side: Near RHS Green 137A. Young foliage under side: Near RHS Green 137A. Mature foliage upper side: Near RHS Green 137A. Mature foliage under side: Near RHS Green 137B.
*Venation*.—Type: Linear with a prominent mid vein on underside. Venation color upper side: Indistinguishable from foliage. Venation color under side: Indistinguishable from foliage.

FLOWER

Natural flowering season: Perpetual flowering.
Inflorescence type and habit: Umbel of 2 flowers, or single occurring flowers.
Flower longevity on plant: 2-3 weeks.
Quantity of flowers: Approximately 50 flowers on a 20 week old plant.
Flowers persistent or self cleaning: Persistent.
Fragrance: Faint to moderate sweet scent.
Inflorescence size:
*Diameter*.—Approximately 6.0 cm.
*Height*.—Approximately 3.5 cm.
Individual flower size:
*Diameter*.—Approximately 3.5 cm.
*Length*.—Approximately 3.0 cm.
Petals, excluding tube:
*Petal arrangement*.—Whorled, multiple whorl.
*Shape*.—Spatulate, with an elongated narrow base and orbicular distal section.
*Base*.—Attenuate.
*Margin*.—Serrated.
*Apex*.—Sharply serrated.
*Length*.—2.5 cm.
*Width*.—1.8 cm.
*Petal quantity*.—Average range 15 to 20.
*Texture*.—Smooth all surfaces.
*Aspect*.—Flat to slightly undulating.
Color:
*When opening*.—Upper surface: Near RHS Red-Purple 63A, but brighter. Base near White 155C. Lower surface: Near RHS Red-Purple 64C. Base near White 155C.
*Fully opened*.—Upper surface: Near RHS Red-Purple 61A. Base near White 155C. Lower surface: Near RHS Red-Purple 64C and 64D. Base near White 155C.
*Fading*.—Upper surface: Near RHS Red-Purple 70B. Base near White 155C. Lower surface: Near RHS Purple 75A and 75B. Base near White 155C.
Tube:
General description: Tube consists of the elongated, unfused base of the petals. Tube shape caused by a fused calyx.
*Length*.—1.6 cm.
*Width*.—1.1 cm.
*Texture*.—Smooth.
Color:
*Fully opened*.—Inner surface: Near RHS Green 138B. Outer surface: Near RHS Green 137C.
Bud:
*Shape*.—Elongated cylinder.
*Length*.—Average 1.8 cm.
*Diameter*.—Average 0.8 cm.
*Color*.—Near RHS Green 143C.
Calyx:
*Length*.—1.5 cm.
*Width*.—7 mm.
*Shape*.—Cylindric.
*Anthocyanin*.—Not present.
Sepals:
*Quantity*.—5.
*Arrangement*.—Fused tube.
*Shape*.—Cylindric.
*Length*.—1.5 cm.
*Width*.—0.4 cm.
*Margin*.—Entire.
*Apex*.—Acute.
*Texture*.—Smooth upper and lower surfaces.
*Color*.—Near RHS Green 143C upper and lower surfaces.
Bracteoles:
*Shape*.—Deltate.
*Quantity per flower*.—4.
*Length*.—Approximately 0.5 cm.
*Width*.—Approximately 0.3 cm.
*Margin*.—Entire.
*Texture*.—Smooth.
*Color*.—Near RHS Green 138A.

Peduncle:
*Length*.—Average 3.1 cm.
*Diameter*.—0.2 cm.
*Color*.—Near RHS Green 138A.
Brachts:
*Number*.—2.
*Shape*.—Deltoid.
*Width*.—4 mm.
*Length*.—5 mm.
*Color*.—RHS Green 138A.
*Orientation*.—Upright.
*Strength*.—Flexible.
*Texture*.—Smooth.
Pedicel:
*Length*.—Average 0.7 cm.
*Diameter*.—0.2 cm.
*Color*.—Near RHS Green 138A.
*Orientation*.—Upright.
*Strength*.—Flexible, elastic.

REPRODUCTIVE ORGANS

Stamens:
*Number*.—Varies from 4 to 8.
*Filament length*.—Approximately 0.9 cm.
Anthers:
*Shape*.—Oblong.
*Length*.—Approximately 0.2 cm.
*Color*.—Near RHS Greyed-Yellow 162B.
*Pollen*.—Not observed.
Pistil:
*Number*.—3.
*Length*.—Approximately 3.2 cm.
*Style*.—Length: Approximately 2.2 cm. Color: Near RHS White N155B.
Stigma:
*Shape*.—Linear, arching.
*Color*.—Near RHS White N155B.
*Ovary shape*.—Oblong.
*Ovary diameter*.—0.6 cm.
*Ovary length*.—1.0 cm.
*Ovary color*.—Near RHS Yellow-Green 145B and 145C.
*Filament color*.—Near RHS White N155B.
*Attachment*.—Dorsifixed.

OTHER CHARACTERISTICS

Seeds and fruits: Not observed to date.
Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.
Temperature tolerance: USDA zones 3 through 10 tolerant.

What is claimed is:
1. A new and distinct cultivar of *Dianthus* plant named 'DCACR08-0' as herein illustrated and described.

* * * * *